United States Patent [19]

Bindra et al.

[11] 4,244,887

[45] Jan. 13, 1981

[54] SUBSTITUTED ω-PENTANORPROSTAGLANDINS

[75] Inventors: Jasjit S. Bindra, Groton; Michael R. Johnson, Gales Ferry, both of Conn.

[73] Assignee: Pfizer Inc., New York, N.Y.

[21] Appl. No.: 68,211

[22] Filed: Aug. 20, 1979

Related U.S. Application Data

[60] Continuation of Ser. No. 602,479, Aug. 6, 1975, abandoned, which is a division of Ser. No. 413,708, Nov. 7, 1973, Pat. No. 4,024,179, which is a continuation-in-part of Ser. No. 304,813, Nov. 8, 1972, abandoned.

[51] Int. Cl.$^3$ .......................................... C07C 177/00
[52] U.S. Cl. .................................. 564/99; 542/429; 260/404; 564/89; 564/91; 564/158
[58] Field of Search ........ 260/556 AC, 559 R, 559 B, 260/404; 542/429

[56] References Cited

U.S. PATENT DOCUMENTS 3,954,741  5/1976  Schaap et al. ...................... 260/556

*Primary Examiner*—Robert Gerstl
*Attorney, Agent, or Firm*—Connolly and Hutz

[57] ABSTRACT

Substituted novel ω-pentanorprostaglandins and various novel intermediates and reagents used in their preparation.

4 Claims, No Drawings

SUBSTITUTED ω-PENTANORPROSTAGLANDINS

CROSS REFERENCE TO RELATED APPLICATIONS

This application is a continuation of application Ser. No. 602,479, filed Aug. 6, 1975 and now abandoned, which in turn is a division of application Ser. No. 413,708, filed Nov. 7, 1973 and now U.S. Pat. No. 4,024,179, which in turn is a continuation-in-part of application Ser. No. 304,813, filed Nov. 8, 1972 and now abandoned.

BACKGROUND OF THE INVENTION

This invention relates to certain novel analogs of the naturally occurring prostaglandins and to various novel intermediates and reagents useful in their preparation. In particular it relates to novel ω-pentanorprostaglandins.

The prostaglandins are C-20 unsaturated fatty acids which exhibit diverse physiological effects. For instance, the prostaglandins of the E and A series are potent vasodilators (Bergstrom, et. al., *Acta Physiol. Scand.* 64:332–33, 1965 and Bergstrom, et al., *Life Sci.* 6:449–455, 1967) and lower systemic arterial blood pressure (vasodepression) on intravenous administration (Weeks and King, *Federation Proc.* 23:327, 1964; Bergstrom, et al., 1965, op. cit.; Carlson, et al., *Acta Med. Scand.* 183:423–430, 1968; and Carlson, et al., *Acta Physiol. Scand.* 75:161–169, 1969). Another well known physiological action for PGE$_1$ and PGE$_2$ is as a bronchodilator (Cuthbert, *Brit. Med. J.* 4:723–726, 1969).

Still another important physiological role for the natural prostaglandins is in connection with the reproductive cycle. PGE$_2$ is known to possess the ability to induce labor (Karim, et al., *J. Obstet Gynaec. Brit. Cwlth.* 77:200–210, 1970), to induce therapeutic abortion (Bygdeman, et al., *Conraception,* 4, 293 (1971) and to be useful for control of fertility (Karim, *Contraception,* 3, 173 (1971)). Patents have been obtained for several prostaglandins of the E and F series as inducers of labor in mammals (Belgian Pat. No. 754,158 and West German Pat. No. 2,034,641), and on PGF$_1$, F$_2$, and F$_3$ for control of the reproductive cycle (South African Pat. No. 69/6089).

Still other known physiological activities for PGE$_1$ are in the inhibition of gastric acid secretion (Shaw and Ramwell, In: *Worcester Symp. on Prostaglandins,* New York, Wiley, 1968, p. 55–64) and also of platelet aggregation (Emmons, et al., Brit. Med. J. 2:468–472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., *Acta. Physiol. Scand.,* 81, 396 (1971) and references cited therein).

It was, of course, considered desirable to create analogs of the prostaglandins which would have physiological activities equivalent to the natural compounds, but in which the selectivity of action and the duration of the activity would be increased. Increased selectivity of action would be expected to alleviate the severe side effects, particularly gastrointestinal side effects, frequently observed following systemic administration of the natural prostaglandins (see *Lancet,* 536, 1971).

SUMMARY OF THE INVENTION

The present invention comprises novel ω-pentanorprostaglandins of the formula:

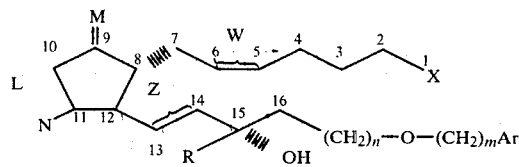

and the C$_{15}$ epimers;
wherein
Ar is phenyl, 3,4-dimethoxyphenyl, 3,4-methylenedioxyphenyl, 3,4,5-trimethoxyphenyl; α- or β-naphthyl or monosubstituted phenyl wherein said substituent is halo, trifluoromethyl, phenyl, lower alkyl or lower alkoxy;
R is hydrogen or lower alkyl;
n and m are each integers from 0 to 3 with the proviso that the sum of n and m does not exceed 3;
W and L are each a single bond or cis double bond;
Z is single bond or trans double bond;
M is keto,

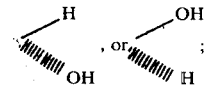

N is hydrogen or α-hydroxyl;
X is selected from:
a first sub-group comprising p-phenyl-phenoxycarbonyl;
a second sub-group comprising tetrazolyl; or
a third sub-group comprising

wherein R" is alkanoyl having from 2–10 carbon atoms or cycloalkanoyl having from 4 to 8 carbon atoms; aryoyl or substituted aryoyl of from 7 to 11 carbon atoms wherein said substituent is methyl, halogen, or methoxy; alkylsulfonyl of from 1 to 7 carbon atoms; arylsulfonyl or substituted arylsulfonyl wherein said substituent is methyl, halogen, or methoxy;
and wherein L, M and N are so selected as to complete the structure of a prostaglandin of the A, E, or F series.

Preferred prostaglandins are those of the formulae:

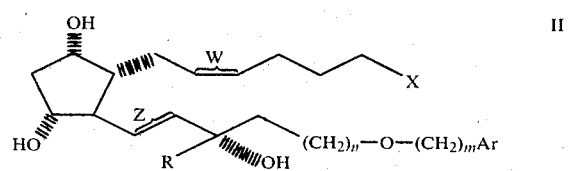

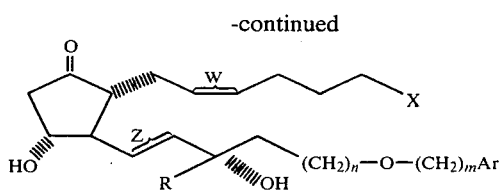

wherein all substituents are as previously defined. Also preferred are the $C_9$ epimers of the compounds of formula II.

Other preferred prostaglandins are as follows:
A compound of formula I wherein n and m are each 0, Ar is phenyl and said prostaglandin is $PGE_2$.
A compound of formula I wherein n and m are each 0, Ar is phenyl, and said prostaglandin is $PGF_{2\alpha}$.
A compound of formula I wherein n is 0, m is 0, Ar is phenyl and said prostaglandin is $PGF_{2\beta}$.
A compound of formula I wherein n is 0, m is 1, Ar is phenyl and said prostaglandin is $PGE_2$.
A compound of formula I wherein n is 0, m is 1, Ar is phenyl and said prostaglandin is $PGF_{2\alpha}$.
A compound of formula II wherein n and m are each 0.
A compound of formula II wherein n and m are each 1.
A compound of formula III wherein n and m are each 0.
A compound of formula III wherein n and m are each 1.

Especially preferred prostaglandins are the following:
A compound according to formula II wherein X is selected from the third sub-group, R'' is acetyl, W is a cis double bond, Z is a trans double bond, R is hydrogen, n and m are each 0, Ar is phenyl.

A compound according to formula II wherein X is selected from the second sub-group, W is a cis double bond, Z is a trans double bond, R is hydrogen, n and m are each 0, Ar is phenyl.

A compound according to formula II wherein X is selected from the third sub-group and R'' is methylsulfonyl, W is a cis double bond, Z is a trans double bond, R is hydrogen, n and m are each 0, Ar is phenyl.

A compound according to formula II wherein X is selected from the third sub-group and R'' is methylsulfonyl, W is a cis double bond, Z is a trans double bond, R is hydrogen, n and m are each 0, and Ar is m-methoxyphenyl.

A compound according to formula III wherein X is selected from the third sub-group, R'' is acetyl, W is a cis double bond, Z is a trans double bond, R is hydrogen, n and m are each 0, Ar is phenyl.

A compound according to formula III wherein X is selected from the third sub-group, R'' is acetyl, W is a cis double bond, Z is a trans double bond, R is hydrogen, n and m are each 0, and Ar is m-methoxyphenyl.

A compound according to formula III wherein X is selected from the second sub-group, W is a cis double bond, Z is a trans double bond, R is hydrogen, n and m are each 0, Ar is phenyl.

A compound according to formula III wherein X is selected from the third sub-group and R'' is methylsulfonyl, W is a cis double bond, Z is a trans double bond, R is hydrogen, n and m are each 0, Ar is phenyl.

Novel intermediates of the formulae below are also a feature of this invention.

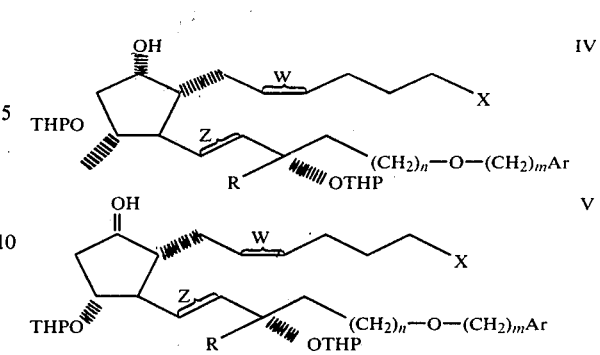

and the $C_9$ and $C_{15}$ epimers thereof;
wherein
Ar is phenyl; 3,4-dimethoxyphenyl; 3,4-methylenedioxyphenyl; 3,4,5-trimethoxyphenyl; α- or β-naphthyl or monosubstituted phenyl wherein said substituent is halo, trifluoromethyl, phenyl, lower alkyl or lower alkoxy;
R is hydrogen or lower alkyl;
THP is 2-tetrahydropyranyl;
n and m are each integers from 0 to 3 with the proviso that the sum of n and m does not exceed 3;
W is a single bond or a cis double bond;
Z is a single bond or trans double bond; and
X is selected from:
a first sub-group comprising p-phenyl-phenoxycarbonyl;
a second sub-group comprising tetrazolyl; or
a third sub-group comprising

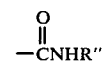

wherein R'' is alkanoyl having from 2–10 carbon atoms or cycloalkanoyl having from 4 to 8 carbon atoms; aryoyl or substituted aryoyl of from 7 to 11 carbon atoms wherein said substituent is methyl, halogen, or methoxy; alkylsulfonyl of from 1 to 7 carbon atoms; arylsulfonyl or substituted arylsulfonyl wherein said substituent is methyl, halogen, or methoxy.

DETAILED DESCRIPTION OF THE INVENTION

The starting material for the various novel compounds of this invention are available commercially or are made by methods well known to those skilled in the art. For example, to make dimethyl 2-oxo-3-phenoxypropylphosphonate, the starting material for the synthesis of the 16-phenoxy prostaglandins, one cools a solution of dimethyl methylphosphonate in tetrahydrofuran to −78° in a dry nitrogen atmosphere and then adds n-butyllithium in hexane dropwise, slowly. After stirring, methyl-2-phenoxy acetate is added dropwise. After 3 to 4 hours at −78° the reaction mixture is warmed to ambient temperature, neutralized with acetic acid and rotary evaporated to a white gel. The gelatinous material is taken up in water, the aqueous phase is extracted in chloroform and the combined organic extracts are backwashed, dried, and concentrated to give the desired product.

To make substituted 16-phenoxy prostaglandins, one requires substituted phenoxy acetic acids which are prepared by condensation of appropriate phenol with a haloacetic acid or ester in presence of base as described by J. M. Petersen, Acta Chem. Scandinavica, 5, 519 (1951) or M. Beroza, Agri. Food Chem., 4, 49 (1956). Thus condensation of bromomethyl acetate with sesmol in presence of sodium methoxide gives the 3,4-methylenedioxyphenoxy acetic acid methyl ester. Similarly, one may prepare p-chlorophenoxy acetic acid, 3,4,5-trimethoxyphenoxy acetic acid and p-phenyl phenoxy acetic acid.

These acids are converted to esters by the usual method and thence into phosphonates as described above for the unsubstituted 16-phenoxy starting compound.

To make the starting material for the 16-phenylpropoxy prostaglandins, one requires the phenylpropoxy acetic acid. This is prepared by method of Rothstein, Bull. Soc. Chim. 51, 691, (1932), converted to the ester and thence to the phosphonate as described for the 16-phenoxy compound.

To prepare the 16-benzyloxyprostaglandins, one requires benzylglycolic acid which is prepared by the method of H. Fisher and B. Gohlke, Helv. Chim. Acta, 16, 1130 (1933) and converted to the ester by standard methods and thence to phosphonate by the method described for 16-phenoxy compound.

When 16-phenethoxy prostaglandins are desired, one makes phenethoxy acetic acid by, for example, the method of Rothstein, Bull. Soc. Chim. 51, 691 (1932), converts it to the ester and thence to the phosphonate as described for the 16-phenoxy compound.

To prepare the 17-phenoxy prostaglandins, 3-phenoxypropionic acid is prepared by the method of S. G. Powell, J.A.C.S., 45, 2708 (1923), converted to the ester and thence to the phosphonate as for the 16-phenoxy compound.

To prepare 18-phenoxy prostaglandins, ethyl 4-phenoxybutyrate is prepared by the method of C. S. Marvel and A. L. Tanenbaum, J.A.C.S., 44, 2645 (1922), and converted to phosphonate as described for the 16-phenoxy case.

To prepare the 19-phenoxy prostaglandins, 5-phenoxyvaleric acid is prepared by the method of A. S. Carter, J. Am. Chem. Soc., 50, 1967 (1928) and converted to the phosphonate as described for the 16-phenoxy case.

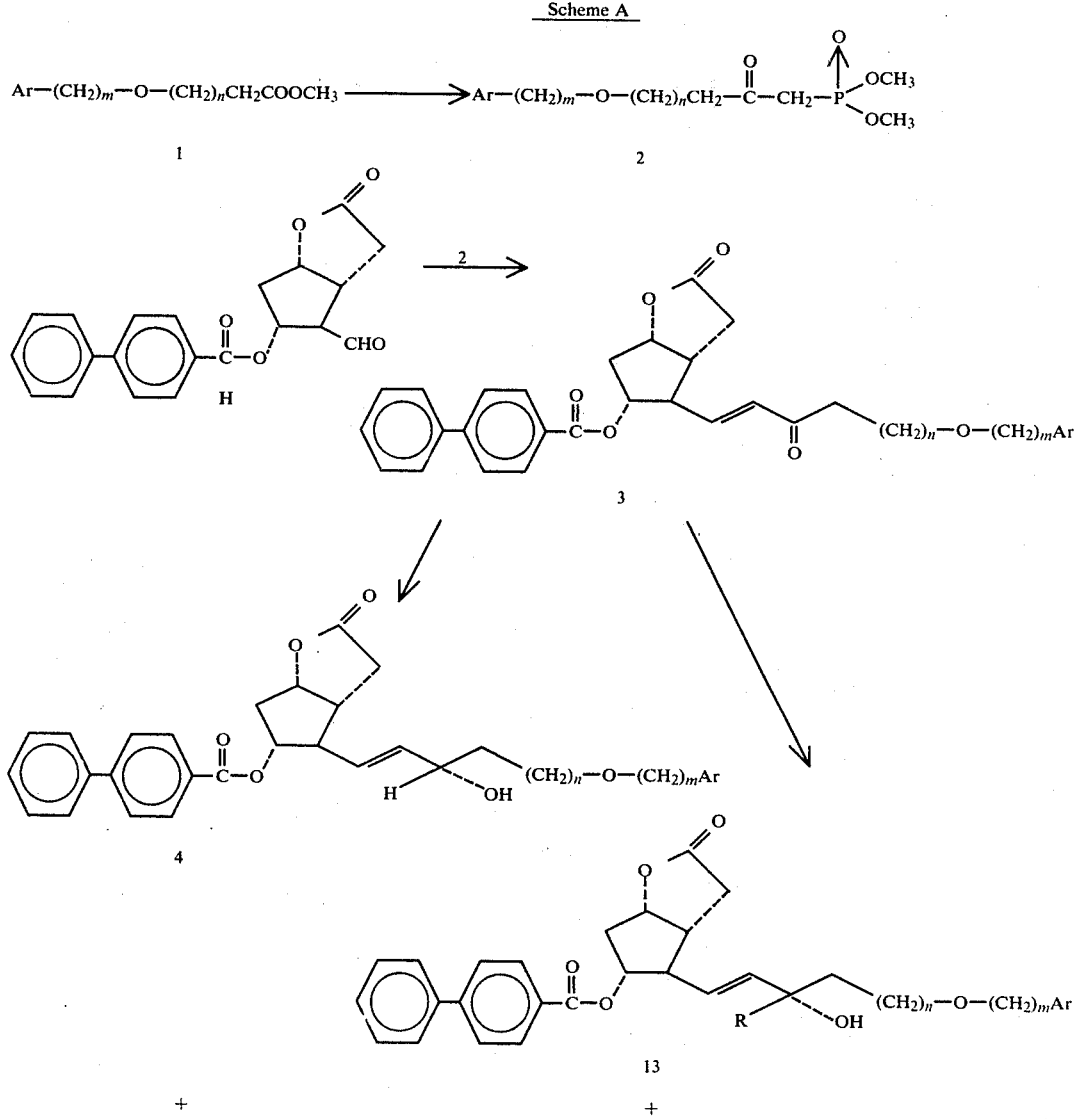

-continued
Scheme A

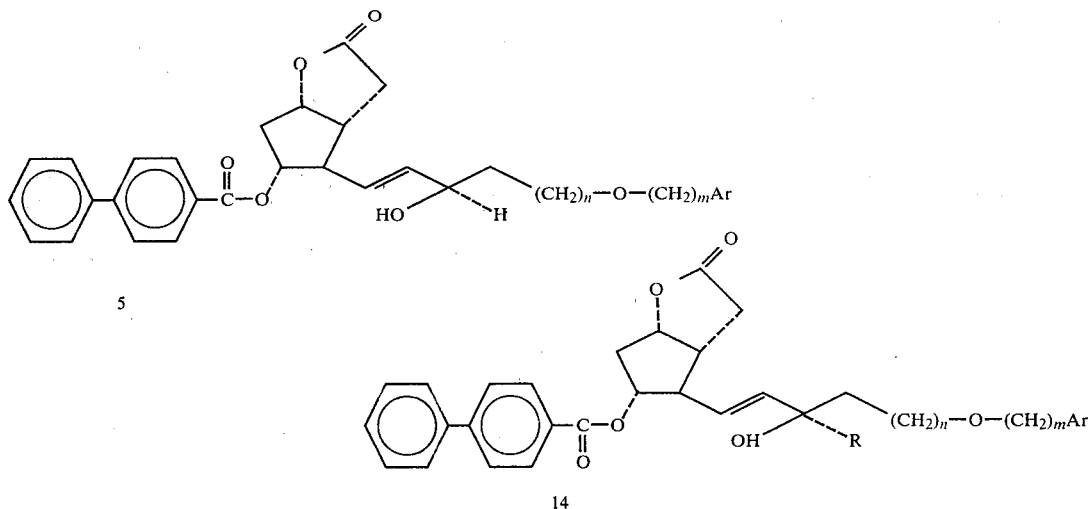

As shown in Scheme A, the first step in the complete synthesis (1→2) is the condensation of the appropriate ester with a dialkyl methylphosphonate to produce ketophosphonate 2. These esters are obtained as previously described.

In 2→3 the ketophosphonate 2 is caused to react with the known [Corey et al., J. Am. Chem. Soc., 93, 1491 (1971)] aldehyde H to produce, after chromatography or crystallization, the enone 3.

The enone 3 can be converted to a mixture of tertiary alcohols 13 and 14 by reaction with the appropriate metal alkyl and the isomeric 13 and 14 can be separated by column chromatography. The enone 3 can be reduced with zinc borohydride or with trialkylborohydrides, such as lithium triethylborohydride, to a mixture of alcohols, 4 and 5 which can be separated as above. In this reaction ethers such as tetrahydrofuran or 1,2 dimethoxy ethane are usually employed as solvents, although occasionally methanol is preferred to ensure specificity of reduction. Further transformations of 4 are shown on Scheme B:

4→6 is a base catalyzed transesterification in which the p-biphenyl-carbonyl protecting group is removed. This is most conveniently conducted with potassium carbonate in methanol or methanol-tetrahydrofuran solvent. 6→7 involves the protection of the two free hydroxyl groups with an acidlabile protecting group. Any sufficiently acid-labile group is satisfactory; however, the most usual one is tetrahydropyranyl, which can be incorporated in the molecule by treatment with dihydropyran and an acid catalyst in an anhydrous medium. The catalyst is usually p-toluenesulfonic acid.

Scheme B

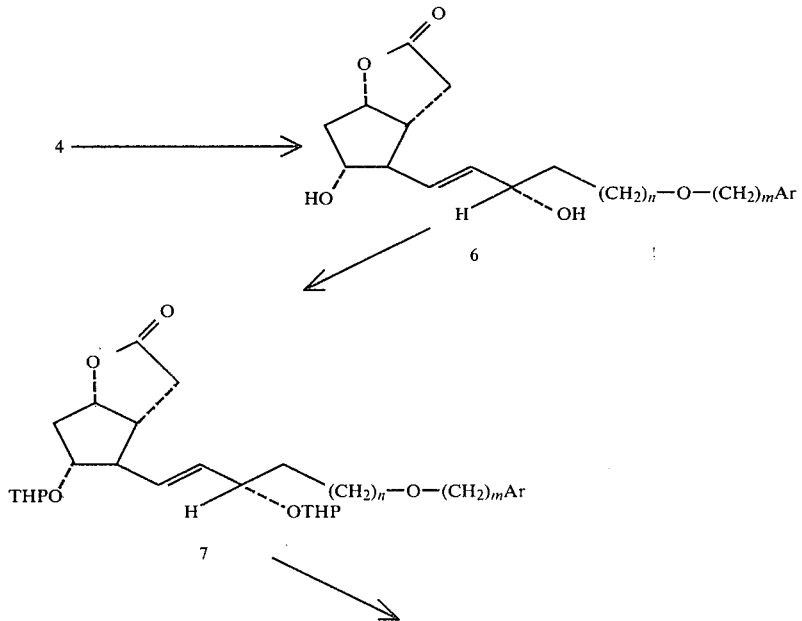

Scheme B

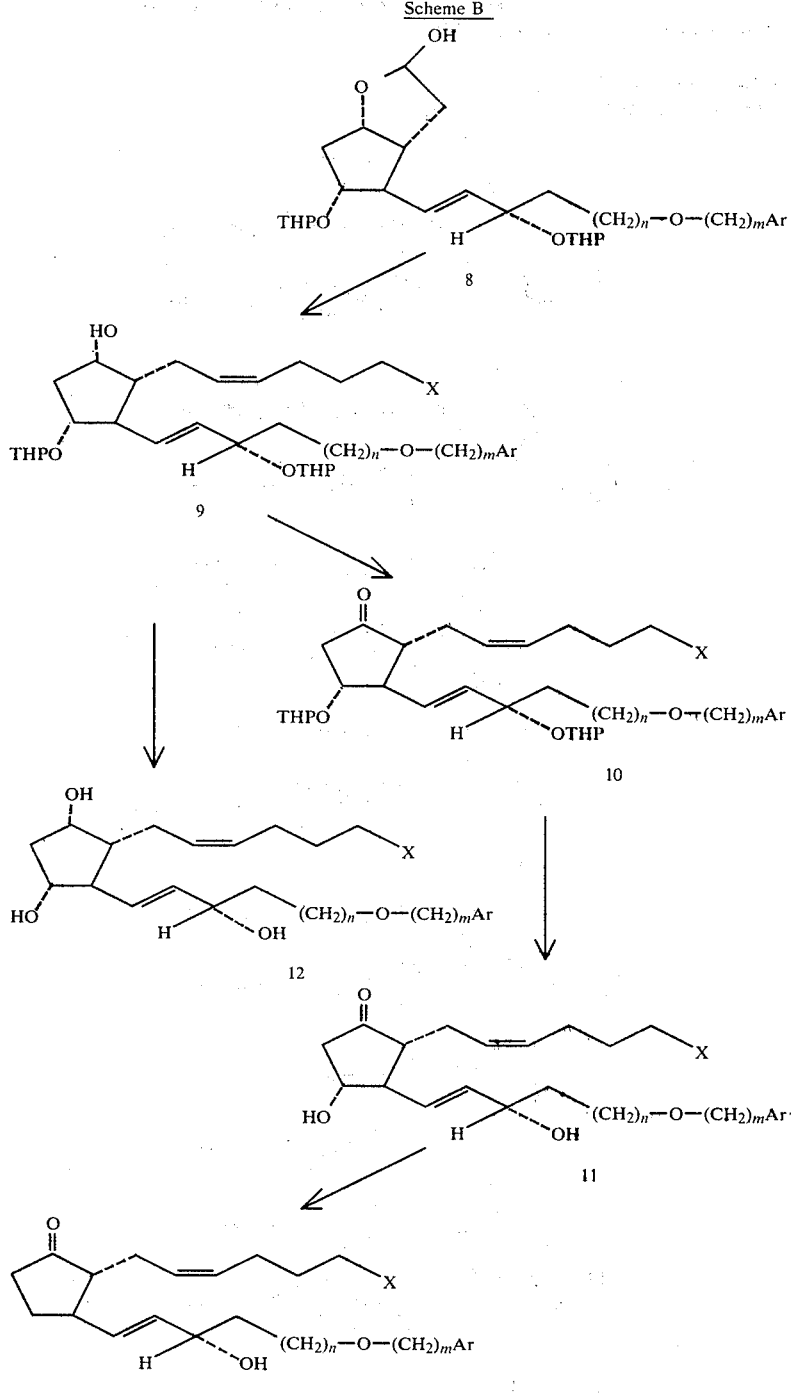

7→8 is a reduction of the lactone 7 to the hemiacetal 8 using diisobutyl aluminum hydride in an inert solvent. Low reaction temperatures are preferred and −60° to −70° C. are usual. However, higher temperature may be employed if over-reduction does not occur, 8 is purified, if desired, by column chromatography. 8→9 is a Wittig condensation in which hemiacetal 8 is reacted with (4-carbohydroxy-n-butyl)triphenylphosphonium bromide in dimethyl sulfoxide, in the presence of sodium methylsulfinyl methide. 9 is purified as above.

The conversion 9→12 is an acidic hydrolysis of the tetrahydropyranyl groups. Any acid may be used which does not cause destruction of the molecule in the course of the removal of the protecting group; however, this is accomplished most often by use of 65% aqueous acetic acid. The product is purified as above.

9→10 is an oxidation of the secondary alcohol 9 to the ketone 10. This may be accomplished using any oxidizing agent which does not attack double bonds;

however, the Jones reagent is usually preferred. The product is purified as above.

10→11 is carried out in the same manner as 9→12. The product is purified as above.

11→15 is an acid-catalyzed dehydration. Any acid may be used for the process which does not cause extensive decomposition of the product, but the most usual procedure consists of dissolving 11 in an excess of 97% formic acid

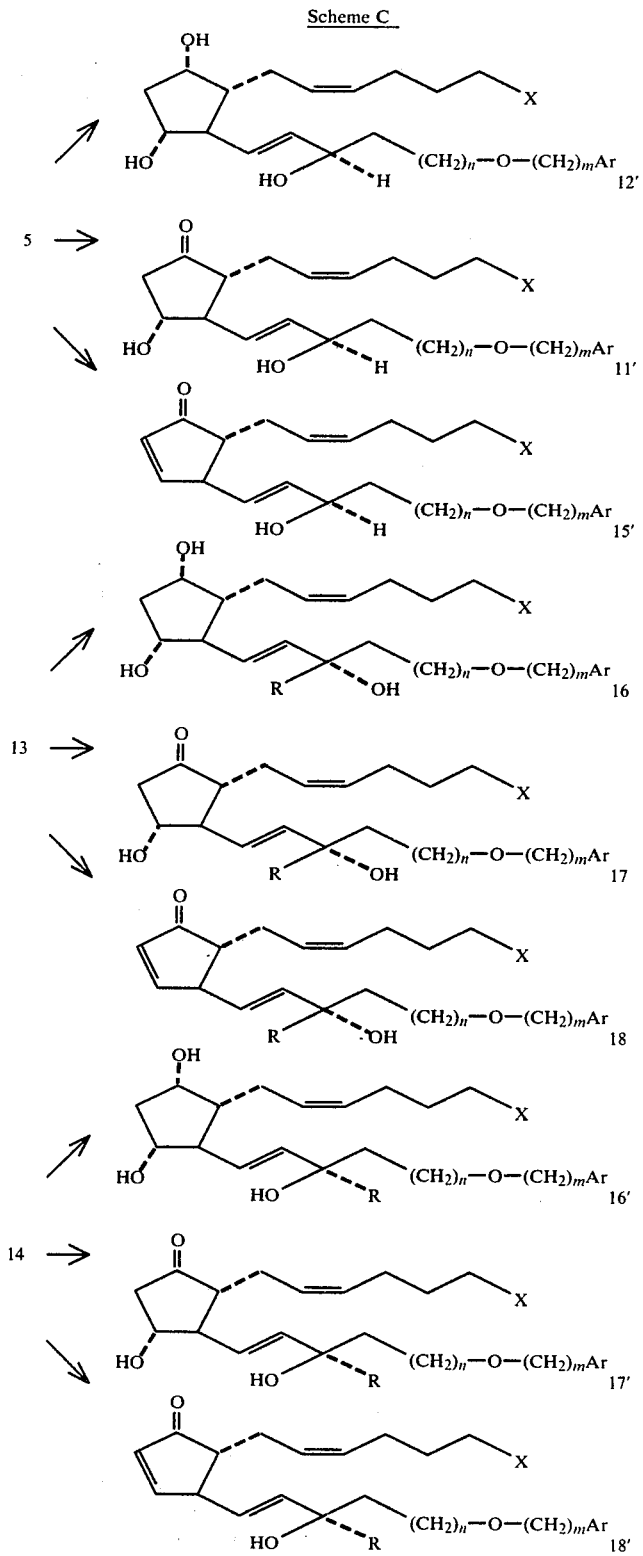

followed by dilution with ice water and extraction of the product after the starting material has been consumed. The product is purified as above.

As is illustrated in scheme C, 5, 13 and 14 may be substituted for 4 in scheme B to provide prostaglandin derivatives 12'–18'.

Scheme D illustrates the synthesis of precursors to the 13,14-dihydro-15-substituted-ω-pentanorprostaglandins.

In 3→19+19' the enone 3 is reduced to the tetrahydro compound through the use of any of the complex metal hydride reducing agents, LiAlH$_4$, NaBH$_4$, KBH$_4$, LiBH$_4$ and Zn(BH$_4$)$_2$. Especially preferred is NaBH$_4$. The products, 19 and 19', are separated from each other by column chromatography.

Furthermore, the compounds 4 and 5 of Scheme A can be reduced catalytically with hydrogen to 19 and 19' respectively. The stage at which the double bond is reduced is not critical, and hydrogenation of 6 or 7 of scheme B will also afford useful intermediates for the 13,14-dihydro prostaglandin analogs of the present invention. This reduction may be achieved with either a homogenous catalyst such as tris(triphenylphosphine)-chlororhodium, or with a heterogeneous catalyst such as platinum, palladium or rhodium. In a similar way the precursors to the 15-lower alkyl-15-substituted-ω-pentanorprostaglandins are synthesized by substituted compounds 13 and 14 for 4 and 5 respectively, in the synthesis just described. The conversion of 19, 19', 20' and 20 to their respective prostaglandins follows the route shown in scheme B when 4 is replaced by 19, 19', 20' and 20 to yield the 13,14-dihydro PGE$_2$, PGA$_2$ and PGF$_2$ series of prostaglandin derivatives containing hydrogen or lower alkyl group at carbon 15.

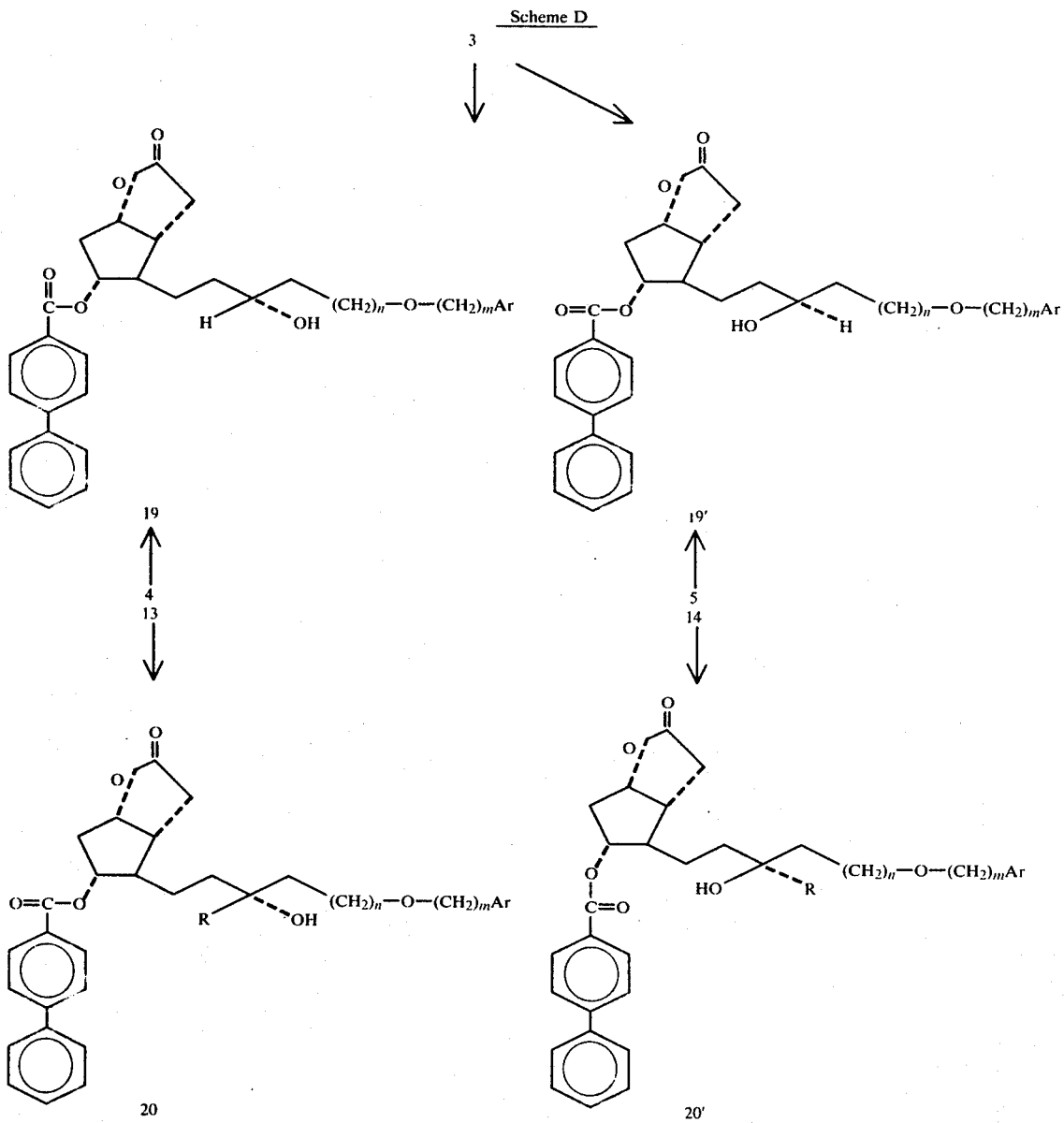

Scheme E illustrates the preparation of the various reduced 15-substituted-ω-pentanorprostaglandin precursors:

19→22 is carried out as illustrated on Scheme B for 4→9. 22 can be used as both a precursor to a 13,14-dihydro 15-substituted-ω-pentanorprostaglandin of the "2-series" or as an intermediate to 23, a precursor to a 13,14-dihydro-15-substituted-ω-pentanorprostaglandin of the "1-series". 22→23 is carried out by catalytic hydrogenation using the catalyst described for the reduction of 4→19 of Scheme D. Intermediates of the type 21 are prepared by selective reduction of the 5,6-cis double bond at low temperature using catalysts such as those described for 4→19 and 17→23. Especially preferred for this reduction is the use of palladium on carbon as a catalyst and a reaction temperature of −20°. Intermediates of the type 21 are not only precursors to 15-substituted-ω-pentanorprostaglandins of the "1-series" through the route 9→15 of scheme B, but also as a precursor to compounds of the type 23 through route already discussed for 22→23.

13,14-position and their $C_{15}$ epimers can be prepared from the appropriately substituted analogs of 9 and 19 whose syntheses follow those of Scheme A and B.

13,14-dihydro-15-lower alkyl-15-substituted-107-pentanorprostaglandins are available from the appropriately substituted precursors via Scheme E.

In the foregoing procedures, where purification by chromatography is desired, appropriate chromatographic supports include neutral alumina and silica gel and 60–200 mesh silica gel is generally preferred. The chromatography is suitably conducted in reaction-inert solvents such as ether, ethyl acetate, benzene, chloroform, methylene chloride, cyclohexane and n-hexane, as further illustrated in the appended examples.

It will be seen that the foregoing formulae depict optically active compounds. It will be clear, however, that the corresponding racemates will exhibit valuable biological activity by virtue of their content of the above-mentioned biologically active optical isomer, and it is intended that such racemates also be embraced by the foregoing formulae herein and in the appended

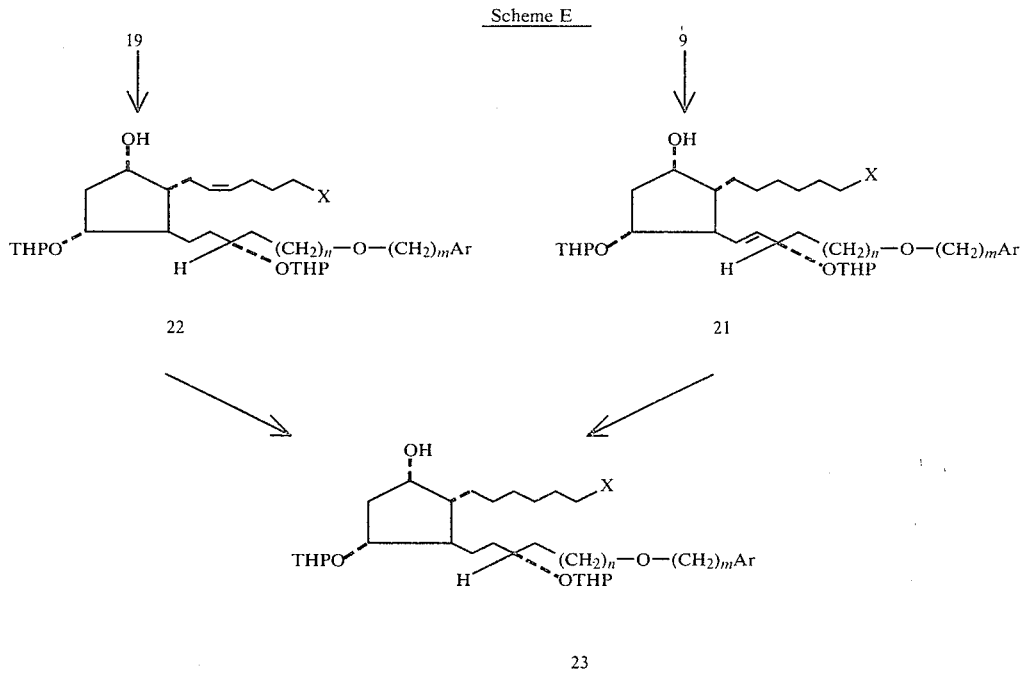

Scheme E

Furthermore, the 15-substituted-ω-pentanorprostaglandins of the $E_1$ and $F_{1\alpha}$ series may be obtained directly from the corresponding prostaglandin analog of the "2-series" by first protecting the hydroxyl by introducing dimethyl isopropyl silyl groups, reducing selectively the cis double bond, and removing the protecting group.

The introduction of the protecting group is usually accomplished by treatment of the prostaglandin analog with dimethyl isopropyl chlorosilane and triethylamine, the reduction is accomplished as discussed above for 9→21 and removal of the protecting group is accomplished by contacting the reduced protected compound with 3:1 acetic acid: water for 10 minutes or until reaction is substantially complete.

The $C_{15}$ epimers of 21, 22 and 23 can be used as precursors to the 15-epi series of prostaglandin derivatives described above, and 15-lower-alkyl-15-substituted-ω-pentanorprostaglandins reduced at the 5,6- and/or the claims. The racemic mixtures are readily prepared by the same methods employed herein to synthesize the optically active species, by mere substitution of corresponding racemic precursors in place of optically active starting materials.

In numerous in vivo and in vitro tests we have demonstrated that the new prostaglandin analogs possess physiological activities comparable to those exhibited by the natural prostaglandins. These tests include, among others, a test for effect on isolated smooth muscle from guinea pig uterus, guinea pig ileum and rat uterus, inhibition of histamine-induced bronchospasm in the guinea pig, and effect on dog blood pressure, inhibition of stress-induced ulceration in the rat, inhibition of gastric acid and pepsin secretion in rat and dog, inhibition of collagen or ADP-induced blood platelet aggregation and abortifacient activity in rats and guinea pigs by luteolytic and non-luteolytic mechanisms.

The physiological responses observed in these tests are useful in determining the utility of the test substance for the treatment of various natural and pathological conditions. Such determined utilities include: antihypertensive activity, bronchodilator activity, antithrombogenic activity, antiulcer activity, smooth muscle activity [useful as an anti-fertility agent, for the induction of labor, and as an abortifacient], and anti-fertility activity through a mechanism not affecting smooth muscle, for example, luteolytic mechanisms, and the synchronization of the estrous cycle in farm animals.

The novel compounds of this invention possess more selectively activity profiles than the corresponding naturally occurring prostaglandins, and in many cases, exhibit a longer duration of action. For example, 16-phenoxy-$\omega$-tetranorprostaglandin $E_2$ while exhibits smooth muscle stimulating activity comparable to $PGE_2$, is inactive in inhibition of histamine-induced bronchospasms in guinea pigs. Furthermore, although the threshold dose of hypotensive response of 16-phenoxy-$\omega$-tetranor $PGE_2$ in dogs is higher than that of $PGE_2$, the duration of action is markedly prolonged relative to $PGE_2$. The 15-substituted-$\omega$-pentanorprostaglandins of the $PGE_0$, $F_{0\beta}$, $F_{1\beta}$, $F_{2\beta}$, and 13,14-dihydro $PGE_{2\beta}$ exhibit similar smooth muscle stimulant activity, whereas the corresponding derivatives of the $A_0$, $A_1$, $A_2$ and 13,14-dihydro $PGA_2$ series have gastric antisecretory/antiulcer activity.

Particularly useful for fertility control, absortion and induction of labor are the 16-phenoxy-$\omega$-tetranorprostaglandins of the $E_2$, $E_{2\alpha}$ and $F_{2\beta}$ series based on especially outstanding smooth muscle stimulating activity, and at the same time reduced blood pressure effects. Similarly, the substituted $\omega$-pentanorprostaglandins of the $PGE_1$, $PGE_{0\alpha}$, $PGF_{1\alpha}$, and 13,14-dihydro $PGF_{2\alpha}$ series are useful for fertility control including abortion and induction of labor on the basis of their smooth muscle stimulant activity. The novel 15-substituted $\omega$-pentanorprostaglandin-13,14-dihydro-$E_2$ analogs can be employed in the treatment of peptic ulcers. The novel prostaglandins with a $\beta$-OH at the 15-position are in general less potent, although frequently more selective than the corresponding $\alpha$-hydroxyl epimers. Additionally, the prostaglandins having a $\beta$-hydroxyl at C-15 are valuable intermediates to prostaglandins having a $\alpha$-hydroxyl at C-15 through a recycling process involving an oxidation and reduction at C-15.

The novel 15 lower alkyl compounds of this invention have the same profile of activity as the prostaglandin analogs of this invention, where R is hydrogen, from which they are derived. Their special utility is concerned with the fact that their duration of action is much increased over the above said compounds, where R is hydrogen, and in such cases where this is essential the 15-lower alkyl compounds are usually preferred. The prostaglandin analogs which have a beta hydroxyl at $C_{15}$ and possess a $C_{15}$ lower alkyl group have action which is similar to their epimers. In some cases, however, the selectivity that these compounds display exceeds that of the epimeric compounds.

The new compounds of this invention can be used in a variety of pharmaceutical formulations which contain the compound, and they may be administered in the same manner as natural prostaglandins by a variety of routes, such as intravenous, oral, intravaginal, intra- and extra-amniotic, among others.

For induction of abortion, tablets or an aqueous suspension or alcoholic solution of the novel 16-substituted $\omega$-tetranorprostaglandins of the E and F series would appropriately be administered at oral doses of about 0.1-20 mg., with 1-7 doses per day being employed. For intravaginal administration a suitable formulation would be lactose tablets or an impregnated tampon of the same agent. For such treatments suitable doses would be from about 0.1-20 mg/dose with 1-7 doses being employed. For intra-amniotic administration a suitable formulation would be an aqueous solution containing 0.05-10 mg/dose with 1-7 doses being employed. For extra-amniotic administration a suitable formulation would be an aqueous solution containing 0.005-1 mg/dose with 1-5 doses being employed. Alternatively, the 16-substituted-$\omega$-tetranorprostaglandins of the E and F series of this invention can be infused intravenously for induction of abortion at doses of 0.05-50 $\mu$g/minute for a period of from about 1-24 hours.

Another use for the novel 16-substituted-$\omega$-tetranorprostaglandins of the E and F series is as an inducer of labor. For this purpose an ethanol-saline solution is employed as an intravenous infusion in the amount of from about 0.1-10 $\mu$g/kg/min for from about 1-24 hours.

Another use for the novel 16-substituted $\omega$-tetranorprostaglandins of the E and F series is for fertility control. For this purpose a tablet is employed for intravaginal or oral administration containing 0.1-20 mg of prostaglandin per dose with 1-7 doses being employed at or following the expected day of menstruation. For synchronization of the estrous cycle in pigs, sheep, cows or horses, a solution or suspension containing 0.03-30 mg/dose of 16-substituted-$\omega$-tetranorprostaglandin of the E and F series is administered subcutaneously from 1-4 days. 16-substituted-$\omega$-pentanorprostaglandins of the A series are useful gastric antisecretory and antiulcer agents, as are the 16-substituted-$\omega$-pentanorprostaglandins of the E series. For treatment of peptic ulcers these compounds are administered preferably orally in the form of capsules or tablets at doses of 0.0001 to 0.1 mg/kg/day.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol, and other known carriers for medicaments. If desired, these pharmaceutical compositions may contain auxiliary substances such as preserving agents, wetting agents, stabilizing agents, or other therapeutic agents such as antibiotics.

The p-biphenyl esters are prepared in the appended examples by simply adding p-phenylphenol to the prostaglandin in methylene chloride in the presence of a dehydrating agent, for example, dicyclc hexylcarbodiimide, and stirring overnight. Although not more potent in in vitro smooth muscle tests, abortifacient evaluation of 16-phenoxy-$\omega$-tetranor $PGE_2$ and $PGF_{2\alpha}$ p-biphenyl esters demonstrated that these p-biphenyl-esters possess physiological activities markedly greater than those of the free acids.

Various other modifications of the upper side chain of the prostaglandins of this invention do not, as a rule, alter the basic biological activity, although they may increase selectivity and duration of action further and reduce toxicity. For example a tetrazoyl moiety may be placed at the $C_1$ position as described in U.S. Ser. No. 177,102 filed Sept. 1, 1971, and in the appended examples. For example, 16-phenoxy-PGE$_2$-tetrazoyl has uterine smooth muscle stimulant activity comparable to 16-phenoxy PGE$_2$ p-biphenyl ester and hence has the same utility; namely, for induction of labor or abortion, and for the inhibition of gastric acid secretion and treatment of peptic ulcers.

Another upper side chain modification which may be made in the prostaglandins of this invention is substitution of the carboxylate moiety at the C$_1$ position by a carboxamide moiety. The methods for preparing these compounds are disclosed in U.S. Ser. No. 260,518 filed June 7, 1972, and in the appended examples. Alternatively, the novel compounds of this invention represented by structures II and III (where X is

and wherein R" is as defined previously), can be prepared from compounds 9 and 10 of Scheme B (or the corresponding 15-epimers or 15-lower alkyl derivatives of 9 and 10) by reaction with appropriate isocyanates, followed by hydrolysis with dilute acid. The utility of N-methylsulfonyl-16-phenoxy PGE$_2$ carboxamide, for example, is the same as that of 16-phenoxy PGE$_2$ p-biphenyl ester.

The following examples are merely illustrative, and in no way limit the scope of the appended claims. In these examples it will be appreciated that all temperatures are expressed in Centigrade, all melting and boiling points are uncorrected.

EXAMPLE I

Dimethyl 2-Oxo-3-phenoxypropylphosphonate

A solution of 33.2 g (268 mmoles) dimethyl methylphosphonate (Aldrich) in 360 ml dry tetrahydrofuran was cooled to −78° in a dry nitrogen atmosphere. To the stirred phosphonate solution was added 118 ml of 2.34 M n-butyllithium in hexane solution (Alfa Inorganics, Inc.) dropwise over a period of 18 minutes at such a rate that the reaction temperature never rose above −65°. After an additional 5 minutes stirring at −78°, 22.2 g (134 mmole) methyl 2-phenoxy acetate was added dropwise at a rate that kept the reaction temperature less than −70° (20 minutes). After 3.5 hours at −78° the reaction mixture was allowed to warm to ambient temperature, neutralized with 14 ml acetic acid and rotary evaporated to a white gel. The gelatinous material was taken up in 175 ml water, the aqueous phase extracted with 100 ml portions of chloroform (3×), the combined organic extracts were backwashed (50 cc H$_2$O), dried (MgSO$_4$), and concentrated (water aspirator) to a crude residue and distilled, b.p. 172°–175° (0.5 mm) to give 24.6 g dimethyl 2-oxo-3-phenoxypropylphosphonate.

The nmr spectrum (CDCl$_3$) showed a doublet centered at 3.75δ (J=11.5 cps, 6H) for

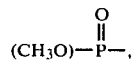

a singlet at 4.7δ (2H) for C$_6$H$_5$O—CH$_2$—CO—, a doublet centered at 3.24δ (J=23 cps, 2H)

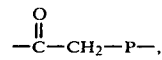

and a multiplet at 6.8–7.5δ (5H) for the aromatic protons.

EXAMPLE II

2-[3α-p-Phenylbenzoyloxy-5α-hydroxy-2β-(3-oxo-4-phenoxy-trans-1-buten-1-yl)cyclopent-1α-yl]Acetic Acid, γ-lactone Dimethyl 2-oxo-3-phenoxypropylphosphonate (5.4 g), 21 mmole) in 200 ml anhydrous ether was treated with 7.9 ml (19 mmole) 2.5 M n-butyllithium in n-hexane (Alfa Inorganics, Inc.) in a dry nitrogen atmosphere at room temperature. After 5 min. of stirring, an additional 400 ml. of anhydrous ether was added followed by 6.0 (17 mmole) 2-[3α-p-phenylbenzoyloxy-5α-hydroxy-2β-formlycylopentan-1α-yl] acetic acid, γ-lactone in one portion and 50 ml anhydrous ether. After 35 minutes the reaction mixture was quenched with 5 ml glacial acetic acid and washed with 100 ml saturated sodium bicarbonate solution (4×), 100 ml water (2×), 100 ml saturated brine (1×), dried (MgSO$_4$) and evaporated to yield 5.2 gm 2-[3α-p-phenylbenzoyloxy-5α-hydroxy-2β-(3-oxo-4-phenoxy-trans-1-buten-1-yl)cyclopent-1α-yl]acetic acid, γ-lactone as a solid after column chromatography (Silica gel, Baker, 60–200 mesh); m.p. 112°–114° after crystallization from methylene chloridehexane.

The ir spectrum (KBr) of the product exhibited absorption bands at 1775 cm$^{-1}$ (strong, 1715 cm$^{-1}$ (strong, 1675 cm$^{-1}$ (medium) and 1630 cm$^{-1}$ (medium) attributable to the carbonyl groups and at 970 cm$^{-1}$ for the trans double bond.

EXAMPLE II

2-[3α-p-Phenylbenzoyloxy-5α-hydroxy-2β-(3α-hydroxy-4-phenoxy-trans-1-buten-1-yl)cyclopent-1α-yl]acetic acid, γ-lactone To a solution of 5.1 g (10.5 mmole) 2-[3α-p-phenylbenzoyloxy-5α-hydroxy-2β-(3-oxo-4-phenoxy-trans-1-buten-1-yl)cyclopent-1α-yl] acetic acid, γ-lactone in 30 ml dry 1,2-dimethoxyethane in a dry nitrogen atmosphere at ambient temperature was added dropwise 11 ml (5.5 mmole) of a 0.5 M zinc borohydride solution. After stirring at room temperature for 2 hours, a saturated sodium bitartrate solution was added dropwise until hydrogen evolution ceased. The reaction mixture was allowed to stir for 5 minutes at which time 250 ml dry methylene chloride was added. After drying (MgSO$_4$) and concentrating (water aspirator) the resultant semisolid was purified by column chromatography on silica gel (Baker "Analyzed" Reagent 60–200 mesh) using ether as eluent. After elution of less polar impurities a fraction containing 896 mg 2-[3α-p-phenylbenzoyloxy-5α-hydroxy-2β-(3α-hydroxy-4-phenoxy-trans 1-buten-1-yl) cyclopent-1α-yl) acetic acid, γ-lactone, a 600 mg fraction of mixed 4 and 5 and finally a fraction (1.5 gm) of 2-[3α-p-phenylbenzoyloxy-5α-hydroxy-2β-hydroxy-4-phenoxytrans-1-buten-yl) cyclopent-1α-yl]acetic acid, γ-lactone.

The ir spectrum (CHCl$_3$) of 4 had strong carbonyl absorptions at 1770 and 1715 cm$^{-1}$ and an absorption at 970 cm$^{-1}$ for the trans double bond.

EXAMPLE IV

2-[3α,5α-Dihydroxy-2β-(3α-hydroxy-4-phenoxy-trans-1-buten-1-yl) cyclopent-1α-yl]acetic acid, γ-lactone A heterogeneous mixture of 846 mg (1.7 mmole) of 2-[3α-p-phenoxybenzoyloxy-5α-hydroxy-2β-(3α-hydroxy-4-phenoxy-trans-1-buten-1-yl)cyclopent-1α-yl]acetic acid, γ-lactone, 10 ml of absolute methanol and 120 mg of finely powdered, anhydrous potassium carbonate was stirred at room temperature for 20 hours, then cooled to 0°. To the cooled solution was added 1.75 ml of 1.0 N aqueous hydrochloric acid. After stirring at 0° for an additional 10 minutes, 10 ml. of water was added with concomitant formation of methyl p-phenyl-benzoate which was collected by filtration. The filtrate was saturated with solid sodium chloride, extracted with ethyl acetate (4×10 ml.), the combined organic extracts were washed with saturated sodium bicarbonate (10 ml.) dried (MgSO$_4$) and concentrated to give 445 mg of viscous, oily 2-[3α,5α-dihydroxy-2β-(3α-hydroxy-4-phenoxy-trans-1-buten-1-yl)cyclopent-1α-yl]acetic acid, γ-lactone.

The ir spectrum (CHCl$_3$) exhibited a strong absorption at 1772 cm$^{-1}$ for the lactone carbonyl and medium absorption at 965 cm$^{-1}$ for the trans-double bond.

EXAMPLE V

2-[5α-Hydroxy-3α-(tetrahydropyran-2-yloxy)-2β-(3α-tetrahydropyran-2-yloxy-4-phenoxy-trans-1-buten-1-yl)cyclopent-1α-yl]acetic acid, γ-lactone To a solution of 445 mg (1.46 mmole) 2-[3d,5α-dihydroxy-2β-(3α-hydroxy-4-phenoxy-trans-1-buten-yl)cyclopent-1α-yl]acetic acid, γ-lactone in 5 ml anhydrous methylene chloride and 0.4 ml of 2,3-dihydropyran at 0° in a dry nitrogen atmosphere was added 5 mg of p-toluenesulfonic acid, monohydrate. After stirring for 15 minutes, the reaction mixture was combined with 100 ml ether, the ether solution washed with saturated sodium bicarbonate (1×15 ml) then saturated brine (1×15 ml), dried (MgSO$_4$) and concentrated to yield 752 mg (>100%) crude 2-[5α-tetrahydropyran-2-yloxy-4-phenoxy-trans-1-buten-1-yl) cyclopent-1α-yl]acetic acid, γ-lactone.

The ir (CHCl$_3$) spectrum had a medium absorption at 970 cm$^{-1}$ for the trans-double bond, and at 1770 cm$^{-1}$ for lactone carbonyl.

EXAMPLE VI

2[5α-Hydroxy-3α-(tetahydropyran-2-yloxy)-2β-(3α-tetrahydrofuran-2-yloxy-4-phenoxy-trans-1-buten-1yl)-cyclopent-1α-yl]acetaldehyde, γ-hemiacetal A solution of 690 mg (1.46 mmole) 2-[5α-hydroxy-3α-(tetrahydropyran-2-yloxy)-2β-(3α-tetrahydropyran-2-yloxy-4-phenoxy-trans-1-buten-1-cyl)cyclopent-1α-yl]acetic acid, γ-lactone in 8 ml dry toluene was cooled to −78° in a dry nitrogen atmosphere. To this cooled solution was added 2.0 ml of 20% diisobutylaluminum hydride in n-hexane (Alfa Inorganics) dropwise at such a rate so that the internal temperature never rose above −65° (15 minutes). After an additional 45 minutes of stirring at −78°, anhydrous methanol was added until gas evolution ceased and the reaction mixture was allowed to warm to room temperature. The reaction mixture was combined with 100 ml ether, washed with 50% sodium potassium tartarate solution (4×20 ml), dried (Na$_2$SO$_4$) and concentrated to yield 613 mg 2-(5α-hydroxy-3α-(tetrahydropyran-2-yloxy)-2β-(3α-tetrahydropyran-2-yloxy-4-phenoxy-trans-1-buten-1-yl)cyclopent-1-yl]acetaldehyde, γ-hemiacetal.

EXAMPLE VII

9α-Hydroxy-11α; 15α-bis-(tetrahydropyran-2-yloxy)-16-phenoxy-cis-5-trans-13-ω-tetranor-prostadienoic acid To a solution of 1.6 gm (3.6 mmole) (4-carbohydroxy-n-butyl)triphenylphosphonium bromide in a dry nitrogen atmosphere in 6.0 ml dry dimethyl sulfoxide was added 3.24 ml (6.5 mmole) of a 2.0M solution of sodium methylsulfinylmethide in dimethyl sulfoxide. To this red ylide solution was added dropwise a solution of 613 mg (1.29 mmole) 2-[5α-hydroxy-3α-(tetrahydropyran-2-yloxy)-2β-(3α-tetrahydropyran-2-yloxy-4-phenoxy-trans-1-buten-1-yl)cyclopent-1α-yl]acetaldehyde, γ-hemiacetal in 5.0 ml dry dimethyl sulfoxide over a period of 20 minutes. After an additional 2 hours stirring at room temperature, the reaction mixture was poured onto ice water. The basic aqueous solution was washed twice with ethyl acetate (20 ml) and acidified to pH 3 with 10% aqueous hydrochloric acid. The acidic solution was extracted with ethyl acetate (3×20 ml) and the combined organic extracts washed once with water (10 ml), dried (MgSO$_4$) and evaporated to a solid residue. This solid residue was triturated with ethyl acetate and the filtrate concentrated to yield 754 mg of 9α-hydroxy-11α,15α-bis-(tetrahydropyran-2-yloxy)-16-phenoxy-cis-5-trans-13-ω-tetranorprostadienoic acid was collected. Infra-red spectrum (CHCl$_3$) displayed a strong band at 1720 cm$^{-1}$ for the carboxyl group.

EXAMPLE VIII

9-Oxo-11α,15α-bis-(tetrahydropyran-2-yloxy)-16-phenoxy-cis-5 trans-13-ω-tetranor-prostadienoic acid To a solution cooled to −10° under nitrogen of 754 mg (1.3 mmole) 9α-hydroxy-11α,15α-bis-(tetrahydropyran-2-yloxy)-16-phenoxy-cis-5-trans-13-ω-tetranorprostadienoic acid in 13 ml reagent grade acetone was added dropwise to 0.56 ml (1.41 mmole) of Jone's reagent. After 20 minutes at −10°, 0.260 ml. 2-propanol was added and the reaction mixture was allowed to stir an additional 5 minutes at which time it was combined with 75 ml ethyl acetate, washed with water (3×10 ml.), dried (MgSO$_4$) and concentrated to give 752 mg. of 9-oxo-11α,15α-bis-(tetrahydropyran-2-yloxy)-16-phenoxy-cis-5-trans-13-ω-tetranorprostadienoic acid, which was chromatographed on silica gel using ethyl acetate as eluent to afford 505 mg. of pure 10.

EXAMPLE IX

9-Oxo-11α,15α-dihydroxy-16-phenoxy-cis-5-trans-13-ω-tetranor prostadienoic acid

A solution of 505 mg (0.9 mmole) 9-oxo-11α,15α-bis-(tetrahydropyran-2-yloxy)-16-phenoxy-cis-5-trans-13-ω-tetranorprostadienoic acid in 6.3 ml. of a 65:35 mixture of glacial acetic acid:water was stirred under nitrogen at 25° for 18 hours then was concentrated by rotary evaporation. The resultant crude oil was purified by column chromatography on silica gel (Mallinckrodt CC-4 100–200 mesh) using ethyl acetate as eluent. After elution of less polar impurities the oily 9-oxo-11α, 15α-dihydroxy-16-phenoxy-cis-5-trans-13-ω-prostadienoic acid weighing 210 mg. was collected.

Ir (CHCl$_3$) displayed a broad band at 1725 cm$^{-1}$ for carbonyl absorptions, and a band at 970 cm$^{-1}$ for the 13,14-trans-double bond.

EXAMPLE X

9α,11α,15α-trihydroxy-16-phenoxy-cis-5-trans-13-ω-tetranorprostadienoic acid

A mixture of 375 mg (0.65 mmole) 9α-hydroxy-11α,15α-bis-(tetrahydropyran-2-yloxy)-16-phenoxy-cis-5-trans-13-ω-tetranor-prostadienoic acid, acetic acid (6.5 ml) and water (3.5 ml) was stirred under nitrogen at room temperature for 20 hours. The resulting clear solution was concentrated under reduced pressure and the residue (380 mg) was dissolved in ethyl acetate. The ethyl acetate solution was washed with brine (20 ml), dried (NaSO$_4$) and concentrated to a clear oil. Chromatography on silica gel (Mallinckrodt CC-7) using chloroform and then ethyl acetate as eluent afforded the desired product, 9α,11α,15α-trihydroxy-16-phenoxy-cis-5-trans-13-ω-tetranor-prostadienoic acid as a colorless oil weighing 98 mg.

EXAMPLE XI

9α-Hydroxy-11α, 15α-bis-(tetrahydropyran-2-yloxy)-16-phenoxy-ω-tetranor-prostanoic acid A mixture of 190 mg (0.33 mmole) 9α-hydroxy-11α,15α-bis(tetrahydropyran-2-yloxy)-16-phenoxy-cis-5-trans-13-ω-tetranorprostadienoic acid, 5% palladium on carbon (150 mg) in methanol (10 ml) is stirred under an atmosphere of hydrogen for 60 hours at room temperature. The mixture is filtered and concentrated to give 9α-hydroxy-11α,15α-bis-(tetrahydropyran-2-yloxy)-16-phenoxy-ω-tetranor-prostanoic acid.

EXAMPLE XII

9α,11α, 15α-Trihydroxy-16-phenoxy-ω-tetranor-prostanoic acid

Hydrolysis of 20 mg 9α-hydroxy-11α,15α-bis-(tetrahydropyran-2-yloxy)-16-phenoxy-ω-tetranor-prostanoic acid is carried out with acetic acid (0.5 ml) and water (0.3 ml) under nitrogen at room temperature for 20 hours. Purification as described in Example X affords pure 9α,11α, 15α-trihydroxy-16-phenoxy-ω-tetranor prostanoic acid.

EXAMPLE XIII

9-Oxo-11α,15α-dihydroxy-16-phenoxy-ω-tetranor-prostanoic acid

A solution of 186 mg (0.3 mmole) of the product of Example XI in 3 ml acetone is oxidized with 0.14 ml (0.35 mmole) of Jones' reagent as described in Example VIII. Isolation of the product and hydrolysis with acetic acid and water at room temperature as described in Example IX gives pure 9-oxo-11α,15α-dihydroxy-16-phenoxy-ω-tetranor-prostanoic acid.

EXAMPLE XIV

9-Oxo-15α-hydroxy-16-phenoxy-cis-5,10,trans-13-ω-tetranor-prostatrienoic acid

A mixture of 52 mg (0.1 mmole) 9-oxo-11α,15α-dihydroxy-16-phenoxy-cis-5-trans-13-ω-tetranor-prostadienoic acid with 0.2 ml 97% formic acid is stirred at 25° for 2.5 hours. About 5 ml ice-water is added to the reaction mixture which is then extracted with ethyl acetate, dried (Na$_2$SO$_4$) and concentrated to give a crude oil. Chromatography of the crude product on silica gel (Mallinckrodt CC-7) using methylene chloride-ethyl acetate as eluent gives the desired 9-oxo-15α-hydroxy-16-phenoxy-cis-5,10,trans-13-ω-tetranor-prostatrienoic acid.

EXAMPLE XV

9-Oxo-15α-hydroxy-16-phenoxy-ω-tetranor-prost-10-enoic acid 9-oxo-11α,15α-dihydroxy-16-phenoxy-ω-tetranor-prostanoic acid is treated with 97% formic acid as described in Example XIV and converted to colorless oily 9-oxo-15α-hydroxy-16-phenoxy-ω-tetranor-prost-10-enoic acid.

EXAMPLE XVI

2-[3α-p-Phenylbenzoyloxy-5α-hydroxy-2β-(3-hydroxy-3-methyl-4-phenoxy-trans-1-buten-1-yl)cyclopent-1α-yl]acetic acid, γ-lactone To a solution of 2-[3α-p-phenylbenzoyloxy-5α-hydroxy-2β-(3-oxo-4-phenoxy-trans-1-buten-1-yl)cyclopent-1α-yl]acetic acid, γ-lactone cooled to −78° in ether-THF, is added dropwise one equivalent of 2 N solution of methyl lithium in ether. After stirring at −78° for 15 minutes the reaction is quenched by addition of glacial acetic acid, sufficient to bring pH up to 7. The mixture is diluted with methylene chloride, washed with water, saturated brine, dried (Na$_2$SO$_4$) and concentrated to give the oily epimeric alcohols. The crude product is purified by column chromatography on silica gel to give the desired 2-[3α-p-phenylbenzyloxy-5α-hydroxy-2β-(3-hydroxy-3-methyl-4-phenoxy-trans-1-buten-1-yl)cyclopent-1α-yl]acetic acid, γ-lactone, which may be converted to give 17 and 17' through steps previously outlined for the preparation of 9-oxo-11α,15α-dihydroxy-16-phenoxy-cis-5-trans-13-ω-tetranor-prostadienoic acid.

EXAMPLE XVII

9β,11α,15α-Trihydroxy-16-phenoxy-5-cis,13-trans-ω-tetranor-prostadienoic acid

To a solution of 50 mg of 9-oxo-11α,15α-dihydroxy-16-phenoxy-cis-5-trans-13-ω-tetranor-prostadienoic acid in 2.5 ml absolute methanol cooled to 0° is added dropwise a soution of 25 mg of sodium borohydride in 1 ml absolute methanol. The reaction mixture is stirred under nitrogen at 0° for 2 hours and then concentrated. The residue is dissolved in methylene chloride, washed with brine, dried (Na$_2$SO$_4$), and is concentrated. Purification of the crude product by silica gel chromatography affords 16-phenoxy PGF$_{2α}$ and the desired 9β-11α,15α-trihydroxy-16-phenoxy-5-cis,13-trans-ω-tetranor prostadienoic acid.

EXAMPLE XVIII

2-[3α-p-Phenylbenzyloxy-5α-hydroxy-2β-(3α-hydroxy-4-phenoxy-but-1-yl)cyclopent-1α-yl]acetic acid, γ-lactone A heterogenous solution of 2.5 g of 2-[3α-p-phenylbenzoyloxy-5α-hydroxy-2β-(3α-hydroxy-4-phenoxy-trans-1-buten-1-yl)cyclopent-1α-yl]acetic acid, γ-lactone and 0.25 g of 5% palladium on charcoal in 30 ml of absolute methanol is stirred under 1 atmosphere of hydrogen for 4 hours. The mixture is then filtered and concentrated to afford 2-[3α-p-phenylbenzoyloxy-5α- hydroxy-2β-(3-oxo-4-phenoxy-but-1-yl)cyclopent-1α-yl]acetic acid, γ-lactone.

To a solution of 1.9 g of the crude hydrogenation product above in 20 ml of absolute methanol is added excess sodium borohydride and the solution is stirred at room temperature under nitrogen for 2 hours, and then concentrated. The residue is diluted with 0.1 N hydrochloric acid and the aqueous layer is extracted with ethyl acetate. The combined organic extracts are washed with saturated brine, are dried ($Na_2SO_4$), and are concentrated. Purification of the crude residue by silica gel chromatography affords 2-[3α-p-phenylbenzyloxy-5α-hydroxy-2β-(3α-hydroxy-4-phenoxy-but-1-yl)cyclopent-1α-yl]acetic acid, γ-lactone and the 3β-hydroxy epimer.

This is converted to the 13,14-dihydro $E_2$ and $F_{2α}$ compounds using methods employed in Examples V through IX.

EXAMPLE XIX

9α-Hydroxy-11α,15α-bis-(tetrahydropyran-2-yloxy)-16-phenoxy-13-trans-ω-tetranorprostenoic acid A heterogeneous mixture of 800 mg of 9α-hydroxy-11α,15α-bis-(tetrahydropyran-2-yloxy)-16-phenoxy-cis-5-trans-13-ω-tetranor-prostadienoic acid and 80 mg of 5% palladium on charcoal in 10 ml of absolute methanol is stirred under 1 atmosphere of hydrogen at −22° for 5 hours. The mixture is then filtered and the filtrate is concentrated to afford 9α-hydroxy-11α,15α-bis-(tetrahydropyran-2-yloxy)-16-phenoxy-13-trans-ω-tetranorprostenoic acid.

Hydrolysis with acetic acid and water in the usual manner affords 16-phenoxy $PGF_{1α}$.

EXAMPLE XX 9-oxo-11α,15α-dihydroxy-16-phenoxy-13-trans-ω-tetranorprostenoic acid A solution of 72 mg 9-oxo-11α,15α-dihydroxy-16-phenoxy-cis-5-trans-13-ω-tetranor-prostadienoic acid in 5 ml of anhydrous ether is treated with 450 mg dimethylisopropyl chlorosilane and 36 mg of triethylamine at room temperature under nitgoren for 48 hours. The reaction mixture is cooled to 0°, methanol is added, and the resulting solution is washed with water, dried ($Na_2SO_4$), and is concentrated. The residue is dissolved in methanol (6 ml) and 30 mg of 5% palladium on charcoal is added. The resulting mixture is stirred at −22° under 1 atmosphere of hydrogen for 4 hours. After filtration and concentration of the filtrate, the residue is stirred with a 65:35 mixture of acetic acid:water for 10 minutes at room temperature. The mixture is diluted with water, extracted with ethyl acetate, dried ($Na_2SO_4$) and concentrated to afford, after purification by silica gel chromatography, 9-oxo-11α,15α-dihydroxy-16-phenoxy-13-trans-ω-tetranorprostenoic acid.

EXAMPLE XXI 4-(Tetrazol-5-yl)butyltriphenylphosphonium bromide

A mixture of 5-bromovaleronitrile (16.2 g., 0.10 mole), triphenylphosphine (26.2 g., 0.10 mole) and toluene (100 ml.) was heated to reflux with stirring under nitrogen for 16 hours. The resulting thick white suspension was cooled to room temperature and filtered. The residue was washed with benzene and air dried to give 33.0 g. of a white, crystalline solid, m.p. 230°–232°, which was 4-cyanobutyltriphenylphosphonium bromide.

Anal. Calc'd for $C_{23}H_{23}BrNP$: C, 65.10; H, 5.47; N, 3.30. Found: C, 65.01; H, 5.40; N, 3.19.

A mixture of the phosphonium salt above (10.0 g., 23.5 mmoles), ammonium chloride (1.60 g., 30.0 mmoles), lithium chloride (0.032 g., 0.76 mmole), sodium azide (1.91 g., 29.3 mmoles), and dimethylformamide (50 ml.) was heated to 127° (oil bath) under nitrogen with stirring for 18 hours. The resulting suspension was cooled and filtered. The residue was washed with dimethylformamide and the combined filtrate and washings were concentrated (aspirator pressure, ca. 45°). The oily residue was crystallized from water at 0° and air dried to give a white crystalline solid (8.11 g.), m.p. 100°–102°. The product was recrystallized from methanol-ether to give white prisms (7.18 g.). m.p. 197°–206°. An analytical sample was prepared by recrystallization from 2-propanol to give a white crystalline powder, m.p. 212°–213°, which was 4-(tetrazol-5-yl) butyltriphenylphosphonium bromide.

Anal. Calc'd for $C_{23}H_{24}H_4PBr$: C, 59.10; H, 5.17; N, 11.99; P, 6.63; Br, 17.09. Found: C, 59.35; H, 5.28; N, 12.31; P, 6.78; Br, 17.26.

EXAMPLE XXII 1-(tetrazol-5-yl)-9α-hydroxy-11α,15α-bis-(tetrahydropyran-2-yloxy)16-phenoxy-cis-5-trans-13-ω-tetranorprostadiene:

To a solution of 4-(tetrazol-5-yl)butyltriphenyl phosphonium bromide (1.49 gm) in a dry nitrogen atmosphere in 6.0 ml. dry DMSO is added 3.24 ml of a 2.0 M solution of sodium methylsulfinylmethide in DMSO. To this solution is added dropwise a solution of 615 mg 2-[5α-hydroxy-3α-(tetrahydropyran-2-yloxy)-2β-(3α-tetrahydropyran-2-yloxy-4-phenoxy-trans-1-buten-1-yl)cyclopent-1α-yl]acetaldehyde, γ-hemiacetal in 5.0 ml dry DMSO over a period of 20 minutes. After an additional 2 hours stirring at room temperature the reaction mixture is poured onto ice water. The basic aqueous solution is acidified with 0.1 N HCl and extracted with ethyl acetate. The residue obtained after evaporation of the solvent is chromatographed, to give pure 1-(tetrazol-5-yl)-9α-hydroxy-11α,15α-bis-(tetrahydropyran-2-yloxy)-16-phenoxy-cis-5-trans-13-ω-tetranor-prostadiene.

EXAMPLE XXIII

[4-(methanesulfonylaminocarbonyl)butyl]triphenylphosphonium bromide

A mixture of 0.950 g (0.01 mole) of methanesulfonamide and 1.80 g. (0.01 mole) of 5-bromovaleric acid chloride was heated on a steam bath until gas evolution ceased (ca. 5 minutes). The brown reaction mixture was allowed to cool and was dissolved in methylene chloride. The methylene chloride solution was treated with Darco, was filtered, and was diluted with hexane with cooling to afford the white, crystalline N-methanesulfonyl-5-bromovaleramide weighing 2.22 g. (86.0% yield) which melted at 88°–89°.

The nmr spectrum ($CDCl_3$) showed a broad singlet at 4.26–3.95 δ for the N—H, a multiplet at 3.66–3.23 for the —C$\underline{H}_2$Br, a singlet at 3.31 δ for the $SO_2$—C$\underline{H}_3$, a multiplet at 2.63–2.20 δ for the —C$\underline{H}_2$CO, and a multiplet at 2.12–1.52 δ for the C$\underline{H}_2$—C$\underline{H}_2$. The ir spectrum ($CHCl_3$) showed a strong absorption at 1720 cm$^{-1}$ attributable to the carbonyl group.

A solution of 2.20 g. (8.57 mmoles) of the N-methanesulfonyl-5-bromovaleramide, prepared as above, 2.24 g. (8.57 mmoles) of triphenylphosphine, and 20 ml. of acetonitrile was heated to reflux under nitrogen overnight. The solution was then concentrated by rotary evaporation and the resultant solid was triturated with hot benzene (4×). The triturated solid was recrystallized from absolute ethanol:ether to afford the white, crystalline [4-(methanesulfonylaminocarbonyl)butyl]-triphenylphosphonium bromide weighing 2.80 g. (63.7% yield) melting at 190°-191°.

The ir spectrum (KBr) of the product exhibited a strong absorption at 5.85μ attributable to the carbonyl group. The nmr spectrum (CDCl$_3$) exhibited a complex multiplet at 8.14-7.27 δ for the aromatic protons, a multiplet at 4.00-3.30 δ for the —C$\underline{H}_2$P, a singlet at 3.12 δ for the —SO$_2$C$\underline{H}_3$, a multiplet at 3.00-2.38 δ for the C$\underline{H}_2$CO, and a multiplet at 2.23-1.38 δ for the C$\underline{H}_2$C$\underline{H}_2$. A titration of the solid product indicated the pKa ½ to be 5.25.

EXAMPLE XXIV p-Biphenyl 9-oxo-11α,15α-dihydroxy-16-phenoxy-cis-5-trans-13-ω-tetranor-prostadienoate To a solution of 50 mg (0.13 mmole) of 9-oxo-11α,15α-dihydroxy-16-phenoxy-cis-5-trans-13-ω-tetranor-prostadienoic acid and 63 mg (0.4 mmole) of p-phenyl-phenol in 10 ml of dry methylene chloride was added 825 mg (0.4 mmole) of dicyclohexylcarbodiimide and the solution stirred overnight at room temperature. After concentration, the crude product was purified by silica gel chromatography to give the desired p-biphenyl ester, m.p. 100°-102°.

Anal.: Calc'd for C$_{36}$H$_{36}$O$_6$: C, 75.53; H, 6.71. Found: C, 75.65; H, 6.83.

EXAMPLE XXV p-Biphenyl 9α,11α,15α-trihydroxy-16-phenoxy-cis-5-trans-13-ω-tetranor-prostadienoate To a solution of 106 mg of 9α,11α,15α-trihydroxy-16-phenoxy-cis-5-trans-13-ω-tetranor-prostadienoic acid and 189 mg of p-phenylphenol in 30 ml dry methylene chloride was added 600 mg of dicyclohexylcarbodiimide and the solution stirred overnight at room temperature. After concentration, the crude product was purified by silica gel chromatography to give 80 mg pure p-biphenyl ester, m.p. 101°-103°.

Anal. Calc'd for C$_{34}$H$_{38}$O$_6$: C, 75.25; H, 7.06. Found: C, 75.38; H, 7.30.

EXAMPLE XXVI

Phenethyl 9-oxo-11α,15α-dihydroxyl-16-phenoxy-cis-5-trans-13-ω-tetranorprostadienoate A mixture of O-phenethyl-N,N'-dicyclohexyl-isourea, prepared by reacting phenethyl alcohol and dicyclohexylcarbodiimide, and 9-oxo-11,15-dihydroxy-16-phenoxy-cis-5-trans-13-ω-tetranorprostadienoic acid in methylene chloride and dimethylformamide is stirred overnight at room temperature. After filtration, concentration and chromatography on silica gel the pure phenethyl ester is obtained.

In a similar fashion are prepared the benzyl, cyclopropyl and cyclooctyl esters using benzyl alcohol, cyclopropanol and cyclooctanol respectively.

EXAMPLE XXVII

Methyl 9α,11α,15α-trihydroxy-16-phenoxy-cis-5-trans-13-ω-tetranorprostadienoate

To an ethereal solution of 100 mg of 9α,11α,15α-trihydroxy-16-phenoxy-cis-5-trans-13-ω-tetranorprostadienoic acid is added an excess of ethereal diazomethane until a yellow color persists. Concentration affords pure methyl 9α,11α,15α-trihydroxy-16-phenoxy-cis-5-trans-——-ω-tetranorprostadienoate.

Similarly, using diazodecane (prepared by oxidation of dodecyl hydrazone) is prepared dodecyl 9α,11α,15α-trihydroxy-16-phenoxy-cis-5-trans-13-ω-tetraorprostadienoate.

EXAMPLE XXVIII

9β,11α,15α-Trihydroxy-16-phenoxy-cis-5-trans-13-ω-tetranorprostadienoic acid tris-hydroxymethylamino methane salt To a solution of 0.70 mmole of 9β,11α,15α-trihydroxy-16-phenoxy-cis-5-trans-13-ω-tetranorprostadienoic acid in 35 ml of dry acetonitrile, heated at 80° is added a solution of 86 mg (0.68 mmole) of tris-hydroxymethylaminomethane in 0.15 ml of water with vigorous stirring. The mixture is allowed to cool to room temperature and 9β,11α,15α-trihydroxy-16-phenoxy-cis-5-trans-13-ω-tetranor-prostadienoic acid tris-hydroxymethylamino methane salt is collected.

EXAMPLE XXIX

9-Oxo-11α,15α-bisformyloxy-16-phenoxy-cis-5-trans-13-ω-tetranorprostadienoic acid To a solution of 0.1 mmole of 9-oxo-11α,15α-dihydroxy-16-phenoxy-cis-5-trans-13-ω-tetranor-prostadienoic acid in 0.5 ml of dry tetrahydrofuran is added 29 mg (0.33 mmole) of formic acetic anhydride and 35 mg (0.33 mmole) of 2,6-lutidine. The solution is stirred for 1 hour under nitrogen at room temperature then 36 mg of water is added. The mixture is stirred at room temperature for additional one hour and diluted with ethyl acetate. The diluted solution is washed with 0.1 N HCl, water and brine, then dried (Na$_2$SO$_4$). Chromatography of the crude product on silica gel affords the desired bisformyloxy compound.

EXAMPLE XXX

9β,11α,15α-Trispivaloyloxy-16-phenoxy-cis-5-trans-13-ω-tetranorprostadienoic acid To a solution of 0.2 mmole of 9β,11α,15α-trihydroxy-16-phenoxy-cis-5-trans-13-ω-tetranor-prostadienoic acid in 1 ml of pyridine is added 120 mg (1.0 mmole) of pivaloyl chloride. The solution is stirred 4 hours at 45° under nitrogen then is cooled to room temperature. Water (40 mg) is added and the mixture stirred 2 hours at room temperature and diluted with ethylacetate. The diluted solution is washed with dilute HCl, water and then brine. Concentration and purification by chromatography on silica gel gave the desired trispivaloyloxy acid.

EXAMPLE XXXI 1-(Tetrazol-5-yl)-9α-hydroxy-11α,15α-bis-(tetrahydropyran-2-yloxy)-16-phenoxy-cis-5-trans-13-ω-tetranor-prostadiene To a solution of 4-(tetrazol-5-yl)butyltriphenyl phosphonium bromide (1.49 g.) in a dry nitrogen atmosphere in 6.0 ml. dry DMSO was added 3.24 ml. of a 2.0 M solution of sodium methylsulfinylmethide in DMSO. To this solution was added dropwise a solution of 615 mg. 2-[5α-hydroxy-3α-(tetrahydropyran-2-yloxy)-2β-(3α-(tetrahydropyran-2-yloxy)-4-phenoxy-trans-1-buten-1-yl)cyclopent-1α-yl]acetaldehyde, γ-hemiacetal in 5.0 ml. dry DMSO over a period of 20 minutes. After an additional 2 hour stirring at room temperature, the reaction mixture was poured onto ice water. The basic aqueous solution was acidified with 0.1 N HCl and extracted with ethyl acetate. The residue obtained after evaporation of the solvent was chromatographed to give 680 mg. pure colorless oily 1-(tetrazol-5-yl)-9α-hydroxy-11α,15α-bis-(tetrahydropyran-2-yloxy)-16-phenoxy-cis-5-trans-13-ω-tetranorprostadiene.

EXAMPLE XXXII 1-(Tetrazol-5-yl)-9α,11α,15α-trihydroxy-16-phenoxy-cis-5-trans-13-ω-tetranor-prostadiene A solution of 300 mg. 1-(tetrazol-5-yl)-9α-hydroxy-11α,15α-bis(tetrahydropyran-2-yloxy)-16-phenoxy-cis-5-trans-13-ω-tetranor-prostadiene in 6 ml. of 65:35 mixture of glacial acetic acid:water was stirred under nitrogen at 25° for 18 hours and then was concentrated by rotary evaporation. The resultant crude oil was purified by column chromatography on silica gel (Mallinckrodt CC-7, 100–200 mesh) using mixtures of chloroform:ethyl acetate as eluant. After elution of less polar impurities the colorless, oily 1-(tetrazol-5-yl)-9α,11α,15α-trihydroxy-16-phenoxy-cis-5-trans-13-ω-tetranor-prostadiene weighing 220 mg. (80% yield) was collected.

EXAMPLE XXXIII 1-(Tetrazol-5-yl)-9-oxo-11α,15α-bis-(tetrahydropyran-2-yloxy)-16-phenoxy-cis-5-trans-13-ω-tetranor-prostadiene To a solution cooled to −15° under nitrogen, of 600 mg. 1-(tetrazol-5-yl)-9α-hydroxy-11α,15α-bis-(tetrahydropyran-2-yloxy)-16-phenoxy-cis-5-trans-13-ω-tetranor-prostadiene in 12 ml. reagent grade acetone was added dropwise 0.6 ml. of Jones' reagent. After 30 minutes at −10°, 0.6 ml. 2-propanol was added and the reaction mixture was allowed to stir an additional 5 minutes at which time it was combined with 75 ml. ethyl acetate, washed with water (3×10 ml.), dried (Na₂SO₄) and concentrated to give 510 mg. of the colorless, oily 1-(tetrazol-5-yl)-9-oxo-11α,15α-bis-(tetrahydropyran-2-yloxy)-16-phenoxy-cis-5-trans-13-ω-tetranorprostadiene.

EXAMPLE XXXIV 1-(Tetrazol-5-yl)-9-oxo-11α,15α-dihydroxy-16-phenoxy-cis-5-trans-13-ω-tetranor-prostadiene A solution of 508 mg. 1-(tetrazol-5-yl)-9-oxo-11α,15α-bis-(tetrahydropyran-2-yloxy)-16-phenoxy-cis-5-trans-13-ω-tetranor-prostadiene in 10 ml. of a 65:35 mixture of glacial acetic acid:water was stirred under nitrogen at 25° for 20 hours and then was concentrated by rotary evaporation. The resultant crude oil was purified by column chromatography on silica gel (Mallinckrodt CC-7 100–200 mesh) using mixtures of chloroform:ethyl acetate as eluants. After elution of less polar impurities the colorless oily 1-(tetrazol-5-yl)-9-oxo-11α,15α-dihydroxy-16-phenoxy-cis-5-trans-13-ω-tetranorprostadiene weighing 240 mg. was obtained.

EXAMPLE XXXV

N-Methanesulfonyl-9α-hydroxy-11α,15α-bis-(tetrahydropyran-2-yloxy)-16-phenoxy-cis-5-trans-13-ω-tetranor-prostadienamide To a solution of 1.7 g. [4-methanesulfonylaminocarbonyl)butyl]triphenylphosphonium bromide in a dry nitrogen atmosphere in 6.0 ml. dry DMSO was added 3.2 ml. (6.5 mmole) of a 2.0 M solution of sodium methylsulfinylmethide in DMSO. To this red ylid solution was added dropwise a solution of 610 mg. (1.29 mmole) 2-[5α-hydroxy-3α(tetrahydropyran-2-yloxy)-2β-(3α-(tetrahydropyran-2-yloxy)-4-phenoxy-trans-1-buten-1-yl)cyclopent-1α-yl]acetaldehyde, γ-hemiacetal in 5 ml. dry DMSO over a period of 20 minutes. After an additional 2 hour stirring at room temperature, the reaction mixture poured onto ice water. The basic aqueous solution was washed twice with ethyl acetate (3×20 ml.) and combined organic extracts washed once with water (10 ml.), dried (Na₂SO₄) and evaporated to an oil. Chromatography on silica gel afforded 684 mg. pure oily N-methanesulfonyl-9α-hydroxy-11α,15α-bis-(tetrahydropyran-2-yloxy)-16-phenoxy-cis-5-trans-13-ω-tetranorprostadienamide.

EXAMPLE XXXVI

N-Methanesulfonyl-9α,11α,15α-trihydroxy-16-phenoxy-cis-5-trans-13-ω-tetranor-prostadienamide A solution of 250 mg. in 5 ml. of 65:35 mixture of glacial acetic acid:water was stirred under nitrogen at 25° for 18 hours and then was concentrated to a crude oil, which was purified by column chromatography on silica gel (Mallinckrodt CC-7, 100–200 mesh) using mixtures of chloroform:ethyl acetate as eluants. After elution of less polar impurities the colorless oily N-methanesulfonyl-9α,11α,15α-trihydroxy-16-phenoxy-cis-5-trans-13-ω-tetranor-prostadienamide weighing 180 mg. was collected. The product was shown to be homogeneous by liquid-liquid chromatography.

EXAMPLE XXXVII

N-Methanesulfonyl-9-oxo-11α,15α-bis-(tetrahydropyran-2-yloxy)-16-phenoxy-cis-5-trans-13-ω-tetranor-prostadienamide To a solution cooled to −10° under nitrogen, of 400 mg. in 8 ml. reagent grade acetone was added dropwise 0.4 ml. of Jones reagent. After 30 minutes at −10°, 0.4 ml. 2-propanol was added and the reaction mixture was allowed to stir an additional 5 minutes at which time it was combined with 60 ml. ethyl acetate, washed with water (3×10 ml.), dried (Na₂SO₄) and concentrated to afford 380 mg. of the colorless oily N-methanesulfonyl-9-oxo-11α,15α-bis-(tetrahydropyran-2-yloxy)-16-phenoxy-cis-5-trans-13-ω-tetranor-prostadienamide.

EXAMPLE XXXVIII

N-Methanesulfonyl-9-oxo-11α,15α-bis-dihydroxy-16-phenoxy-cis-5-trans-13-ω-tetranor-prostadienamide A solution of 260 mg. in 6 ml. of a 65:35 mixture of glacial acetic acid:water was stirred under nitrogen at 25° for 20 hours and then was concentrated to a crude oil which was purified by column chromatography on silica gel (Mallinckrodt CC-7, 100–200 mesh) using mixtures of chloroform:ethyl acetate as eluants. After elution of less polar impurities the colorless N-methanesulfonyl-9-oxo-11α,15α-bis-dihydroxy-16-phenoxy-cis-5-trans-13-ω-tetranor-prostadienamide weighing 130 mg. was obtained. The product crystallized from ether as colorless crystals, m.p. 76°.

EXAMPLE XXXIX

9β,11α,15α-Trihydroxy-16-phenoxy-cis-5-trans-13-ω-tetranor-prostadienoic acid

To a stirred solution of 0.18 g. (0.47 mmole) 9-oxo-11α,15α-dihydroxy-16-phenoxy-cis-5-trans-13-ω-tetranor-prostadienoic acid in MeOH (20 ml.) at 0° was added a cold solution of 0.06 g. $NaBH_4$ in MeOH (10 ml). After 1 hour at 0°, the reaction was quenched by addition of water (4 ml.) and concentrated under reduced pressure. The residue was acidified with 10% HCl to pH 3, extracted with ethyl acetate, dried ($Na_2SO_4$) and concentrated. Chromatography on 20 g. silica gel (CC-7) and elution with methanol-benzene afforded pure 9β,11α,15α-trihydroxy-16-phenoxy-cis-5-trans-13-ω-tetranor-prostadienoic acid, as a colorless oil, homogenous on t.l.c., rf 0.25 ($C_6H_6$—dioxan—$HCO_2H$, 15:5:2).

EXAMPLE XL

N-Benzoyl 9-oxo-11α,15α-dihydroxy-5-cis-13-trans-16-phenoxy-ω-tetranorprostadienamide To 1.0 m mole of 9-oxo-11α,15α-bis-(tetrahydropyran-2-yl oxy)-16-phenoxy-cis-5-trans-13-ω-tetranor-prostadienoic acid (Example VIII) in 40 ml. THF is added 2 ml. triethylamine. After 15 minutes of stirring at room temperature 10.0 ml of 0.1 molar benzoylisocyanate in THF is added. After a further hour of stirring, the reaction mixture is neutralized with acetic acid and the solvent removed by evaporation (in vacuo). The resultant residue is taken up in methylene chloride and washed successively with water and sodium bicarbonate to yield, after drying and solvent evaporation, N-benzoyl 9-oxo-11α,15α-bis-(tetrahydropyran-2-yl oxy)-16-phenoxy-cis-5-trans-13-ω-tetranor-prostadienamide. This intermediate is then hydrolized overnight with acetic acid/water (as in Example IX) and purified by column chromatography to give the desired N-benzoyl-9-oxo-11α,15α-dihydroxy-5-cis-13-trans-16-phenoxy-ω-tetranorprostadienamide.

EXAMPLE XLI

N-Methanesulfonyl 9-oxo-11α,15α-dihydroxy-5-cis-13-trans-16-phenoxy-ω-tetranorprostadienamide To 1.0 m mole of 9-oxo-11α,15α-bis-(tetrahydropyran-2-yl oxy)-16-phenoxy-cis-5-trans-13-ω-tetranor-prostadienoic acid (Example VIII) in 40 ml. THF is added 2 ml triethylamine. After 15 minutes of stirring at room temperature 10.0 ml of 0.1 molar methanesulfonylisocyanate in THF is added. After a further hour of stirring, the reaction mixture is neutralized with acetic acid and the solvent removed by evaporation (in vacuo). The resultant residue is taken up in methylene chloride and washed successively with water and sodium bicarbonate to yield, after drying and solvent evaporation, N-methanesulfonyl 9-oxo-11α,15α-bis (tetrahydropyran-2-yl oxy)-16-phenoxy-cis-5-trans-13-ω-tetranorprostadienamide. This intermediate is then hydrolized overnight with acetic acid/water (as in Example IX) and purified by column chromatography to give the desired N-methanesulfonyl 9-oxo-11α,15α-dihydroxy-5-cis-13-trans-16-phenoxy-ω-tetranorprostadienamide.

EXAMPLE XLII

N-Acetyl-9α-hydroxy-11α,15α-bis-(tetrahydropyran-2-yloxy)-16-phenoxy-cis-5-trans-13-ω-tetranor-prostadienamide To a solution of 5.32 g [4-acetamido carbonyl)butyl]-triphenyl phosphonium bromide in a dry nitrogen atmosphere in 10 ml dry DMSO was added 17.7 ml of a 2.0 M solution of sodium methylsulfinyl methide in DMSO. To this red ylid solution was added dropwise a solution of 0.524 g (1.1 mmoles) 2-[5α-hydroxy-3α-(tetrahydropyran-2-yloxy)-2β-(3α-(tetrahydropyran-2-yloxy)-4-phenoxy-trans-1-buten-1-yl)cyclopen-1α-yl]acetaldehyde, γ-hemiacetal in 10 ml dry DMSO over a period of 20 minutes. After an additional 2 hours stirring at room temperature, the reaction mixture was poured onto ice water. The basic aqueous solution was washed twice with ethyl acetate (3×25 ml) and combined organic extracts washed once with water (10 ml), dried ($Na_2SO_4$) and evaporated to an oil. Chromatography on silica gel afforded 0.66 gm pure oily N-acetyl-9α-hydroxy-11α,15α-bis-(tetrahydropyran-2-yloxy)-16-phenoxy-cis-5-trans-13-ω-tetranor-prostadienamide.

EXAMPLE XLIII

N-Acetyl-9α,11α,15α-trihydroxy-16-phenoxy-cis-5-trans-13-ω-tetranor-prostadienamide A solution of 0.39 g of N-acetyl-9α-hydroxy-11α,15α-bis-(tetrahydropyran-2-yloxy)-16-phenoxy-cis-5-trans-13-ω-tetranorprostadienamide in 5 ml of 65:35 mixture of glacial acetic acid:water was stirred under nitrogen at 25° for 18 hours and then was concentrated to a crude oil, which was purified by column chromatography on silica gel (CC-7), using mixtures of chloroform:ethyl acetate as eluant. After elution of less polar impurities the colorless oil N-acetyl-9α,11α,15α-trihydroxy-16-phenoxy-cis-5-trans-13-ω-tetranor-prostadienamide weighing 95 mg. was collected.

EXAMPLE XLIV

N-Acetyl-9-oxo-11α,15α-bis(tetrahydropyran-2-yloxy)-16-phenoxy-cis-5-trans-13-ω-tetranor-prostadienamide To a solution cooled to −10° under nitrogen, of 394 mg N-acetyl-9α-hydroxy-11α,15α-bis(tetrahydropyran-2-yloxy)-16-phenoxy-cis-5-trans-13-ω-tetranor-prostadienamide in 10 ml reagent-grade acetone was added dropwise 0.27 ml of Jones reagent. After 30 minutes at −10°, 0.4 ml 2-propanol was added and the reaction mixture was allowed to stir an additional 5 minutes at which time it was combined with 60 ml ethyl acetate, washed with water (3×10 ml), dried ($Na_2SO_4$) and concentrated to afford 390 mg of colorless oily N-acetyl 9-oxo-11α,15α-bis-(tetrahydropyran-2-yloxy)-16-phenoxy-cis-5-trans-13-ω-tetranor-prostadienamide.

EXAMPLE XLV

N-Acetyl-9-oxo-11α,15α-bis-dihydroxy-16-phenoxy-cis-5-trans-13-ω-tetranor-prostadienamide A solution of 390 mg of N-acetyl-9-oxo-11α,15α-bis-(tetrahydropyran-2-yloxy)-16-phenoxy-cis-5-trans-13-ω-tetranorprostadienamide in 8 ml of a 65:35 mixture of glacial acetic acid:water was stirred under nitrogen at 25° for 20 hours and then was concentrated to a crude oil which was purified by column chromatography on silica gel using mixtures of chloroform ethyl acetate as eluants. After elution of less polar impurities the colorless oily N-acetyl-9-oxo-11α,15α-bis-dihydroxy-16-phenoxy-cis-5-trans-13-ω-tetranor-prostadienamide weighing 76 mg.

What is claimed is:

1. A compound selected from the group consisting of

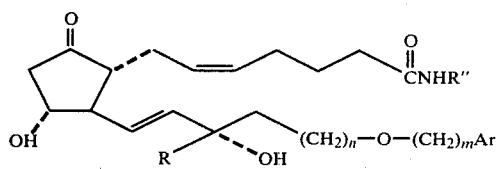

and its $C_{15}$ epimer wherein Ar is phenyl, 3,4-dimethoxyphenyl, 3,4-methylenedioxyphenyl, 3,4,5-trimethoxyphenyl; α- or β-naphthyl or monosubstituted phenyl wherein said substituent is halo, trifluoromethyl, phenyl, lower alkyl, or lower alkoxy;

R is hydrogen or lower alkyl;

n and m are each integers from 0 to 3 with the proviso that the sum of n and m does not exceed 3 and R" is alkanoyl having from 2–10 carbon atoms or cycloalkanoyl having from 4 to 8 carbon atoms; aroyl or substituted aroyl of from 7 to 11 carbon atoms wherein said substituent is methyl, halogen, or methoxy; alkylsulfonyl of from 1 to 7 carbon atoms; arylsulfonyl or substituted arylsulfonyl wherein said substituent is methyl, halogen or methoxy.

2. A compound of claim 1 wherein Ar is phenyl; R is hydrogen; n and m are each 0 and R" is acetyl.

3. A compound of claim 1 wherein Ar is m-methoxyphenyl; R is hydrogen; n and m are each 0 and R" is acetyl.

4. A compound of claim 1 wherein Ar is phenyl. R is hydrogen; n and m are each 0 and R" is methylsulfonyl.

* * * * *